United States Patent [19]

Cathey et al.

[11] Patent Number: 5,798,215
[45] Date of Patent: Aug. 25, 1998

[54] DEVICE FOR USE IN ANALYTE DETECTION ASSAYS

[75] Inventors: Cheryl A. Cathey, Gaithersburg, Md.; Tom Saul, El Granada, Calif.; Nicole D. Bloom, San Francisco, Calif.; Hans O. Ribi, Hillsborough, Calif.; Henry L. Schwartz, San Francisco, Calif.; Jeffrey B. Langford, Corvallis, Oreg.; David J. Paul, Scotts Valley, Calif.

[73] Assignee: Biocircuits Corporation, Sunnyvale, Calif.

[21] Appl. No.: 420,987

[22] Filed: Apr. 6, 1995

Related U.S. Application Data

[63] Continuation-in-part of Ser. No. 296,489, Aug. 24, 1994, Pat. No. 5,660,993, which is a continuation-in-part of Ser. No. 179,749, Jan. 7, 1994, Pat. No. 5,503,985, which is a continuation-in-part of Ser. No. 19,469, Feb. 18, 1993, Pat. No. 5,399,486.

[51] Int. Cl.[6] .......................... G01N 33/53; G01N 33/543; G01N 33/558
[52] U.S. Cl. .................. 435/7.9; 422/55; 422/57; 422/58; 422/61; 435/7.92; 435/7.93; 435/7.94; 435/287.1; 435/287.2; 435/288.4; 435/288.5; 435/288.7; 435/810; 436/514; 436/518; 436/524; 436/527; 436/528; 436/164; 436/172; 436/537; 436/805; 436/807; 436/808; 436/810
[58] Field of Search ................... 422/55, 57, 58, 422/61, 64; 435/7.9, 7.92, 7.93, 7.94, 287.1, 287.2, 288.4, 288.5, 288.7, 810; 436/514, 518, 524, 527, 528, 800, 805, 807, 808, 810, 164, 172, 537

[56] References Cited

U.S. PATENT DOCUMENTS

| | | |
|---|---|---|
| 4,012,198 | 3/1977 | Finter et al. |
| 4,426,451 | 1/1984 | Columbus |
| 4,855,240 | 8/1989 | Rosenstein et al. |
| 4,859,421 | 8/1989 | Apicella |
| 4,918,025 | 4/1990 | Grenner |
| 5,028,142 | 7/1991 | Ostoich et al. |
| 5,053,197 | 10/1991 | Bowen |
| 5,061,446 | 10/1991 | Guigan |
| 5,079,142 | 1/1992 | Coleman et al. |
| 5,133,937 | 7/1992 | Frackleton et al. |
| 5,167,922 | 12/1992 | Long |
| 5,198,368 | 3/1993 | Khalil et al. |
| 5,207,988 | 5/1993 | Lucas |
| 5,217,905 | 6/1993 | Marchand et al. |
| 5,223,219 | 6/1993 | Subramanian et al. |
| 5,399,486 | 3/1995 | Cathey et al. ............ 435/7.9 |
| 5,503,985 | 4/1996 | Cathey et al. ............ 435/7.9 |

FOREIGN PATENT DOCUMENTS 0-430 248   5/1991   European Pat. Off.

*Primary Examiner*—Christopher L. Chin
*Attorney, Agent, or Firm*—Cooley Godward LLP

[57] ABSTRACT

A device and method for its use in diagnostic assays are provided. The device comprises at least one assay path, where an assay path includes a main flow path and at least one side reagent channel. The main flow path begins at a sample addition port, continues through a main reagent area into an incubation area and ends in a waste area. In fluid communication with the main flow path is at least one side reagent channel that begins at a liquid addition port, continues through a side reagent area and ends in said main channel at a region between the main reagent and waste areas, usually upstream from the incubation area. Agitation means may be included in at least one of the main and side reagent areas and/or the incubation area. At least one fluid interruption means located at various positions along the main and side reagent channels upstream from the incubation area provide for control over reagent interaction and fluid flow through the device. Applications in which the device finds use include diagnostic assays employing signal producing systems based on the interactions of specific binding pair members, where an optical signal is related to the presence of analyte.

34 Claims, 8 Drawing Sheets

DEVICE FOR USE IN ANALYTE DETECTION ASSAYS

CROSS-REFERENCE TO RELATED APPLICATIONS

This application is a continuation-in-part of application Ser. No. 08/296,489, filed Aug. 24, 1994, now U.S. Pat. No. 5,660,993; which is a continuation-in-part of application Ser. No. 08/179,749, filed Jan. 7, 1994, now U.S. Pat. No. 5,503,985; which is a continuation-in-part of application Ser. No. 08/019,469 filed Feb. 18, 1993, now U.S. Pat. No. 5,399,486.

INTRODUCTION

TECHNICAL FIELD

The technical field of this invention is analyte detection devices.

BACKGROUND

Despite the numerous strides that have been made in the last two decades in the development of reagents and instruments for use in diverse analyte detection assays, efforts continue to make these applications more accurate, less complex and more available to non-technical personnel in a wide variety of environments. For example, there is continuing interest in being able to carry out individual assays by non-technical personnel at such sites as doctor's offices, clinics, the home, rest homes, and the like. In order to ensure that non-technical individuals may accurately perform these assays, it is essential that the protocols be simple and that there be few, if any, measurements. Further, the readings should be relatively automatic.

In designing a device for use in analyte detection assays, it is often desirable to have a disposable device which can be used individually for a particular application and then discarded. The disposable device can provide the various reagent members which are necessary for the application to be performed, serve to ensure the appropriate mixing of these reagents and, where appropriate, allow for the proper fitting of the device into an automated instrument for reading the assay results. Thus, in using the device, the operator need only add sample and then read the result. In this manner, reliable assay determinations may be made rapidly and with a minimum opportunity for error in quantitation.

Clinical laboratories also provide many opportunities for use of such devices. Frequently, particular analytes may be determined only a few times in any one day, so that individual assays will be the most efficient method of performing a particular analyte determination. Where one can use a disposable device which only requires the addition of the sample to the disposable device, significant savings in labor may be realized, because individuals of high technical qualification would not be required for operation of the assay and the accuracy of the analyte determination would be relatively assured.

In response to this need for devices which can be used in a variety of assays, the industry has responded with devices which allow for the performance of the application protocol, with minimal measurement and input from the operator, while allowing for sensitive and accurate detection of the amount of analyte in a sample. See U.S. Pat. Nos. 4,012,198; 4,426,451; 4,855,240; 4,859,421; 4,918,025; 5,198,368; 5,217,905; 5,223,219 and EP-A 430 248.

Despite the development of such devices, there are problems with currently available designs. Long-standing difficulties have included problems with efficiently mixing reagents with sample, problems in efficient washing to remove unbound reagents from a measurement area, problems in controlling the fluid flow through the assay device, problems in controlling the timing of interaction between reagent members of a particular assay in the device, and the like. Furthermore, where a disposable device is desired, problems have been encountered in designing a device which has a basic design that is sufficiently adaptable for use in a variety of different assays, where such a basic design would provide for a reduction in manufacturing costs.

Thus, there is a need for the development of improved devices for use in analyte detection assays. The improved devices should provide for increased ease and simplicity of use, while consistently providing for a reliable result. The improved devices should also provide for improved control and reproducibility over reagent interaction and fluid flow through the device. Furthermore, the devices should have a structural configuration that is adaptable for use in a wide variety of diverse assays and other protocols, thereby reducing manufacturing costs while expanding the possible applications in which the device may be employed.

RELEVANT LITERATURE

Enzyme immunoassays are described in: Tijssen, Practice and Theory of Enzyme Immunoassays (Elsevier) 1985; Wisdom, "Recent Progress in the Development of Enzyme Immunoassays," Ligand Rev. (1981) 3: 44–49; and Ishikawa, "Development and Clinical Applications of Sensitive Enzyme Immunoassays for Macromolecular Antigens-A Review," Clin. Biochem. (1987) 20: 375–385.

Fluorescence Immunoassays are described in: Smith et al., "A Review of Fluoroimmunoassay and Immunofluorometric Assay," Ann. Clin. Biochem. (1981) 18: 253–274; Hammila, "Fluoroimmunoassays and Immunofluorometric Assays," Clin. Chem. (1985) 31: 359–370; Diamandis, "Immunoassays with Time-Resolved Fluorescence Spectroscopy: Principles and Applications," Clin. Biochem. (1988) 21: 139–150.

Chemiluminescent Immunoassays are described in: Kricka & Thorpe, "Luminescent Immunoassays," Ligand Rev. (1981) 3: 17–24; Seitz, "Immunoassay Labels Based on Chemiluminescence and Bioluminescence," Clin. Biochem. (1984) 17: 120–125; Weeks & Woodhead, "Chemiluminescence Immunoassay," J. Clin. Immunoassay (1984) 7: 82–89. Fluorescence polarization techniques are described in: DeGrella, "Fluorescence Polarization: A Review of Laboratory Applications," Amer. Biotech. Lab. (1988) 6: 29–34; Jolley et al., "Fluorescence Polarization Immunoassay. III. An Automated System for Therapeutic Drug Determination," Clin. Chem. (1981) 27: 1575–1579; Dandliker et al., "Fluorescence Methods for Measuring Reaction Equilibria and Kinetics," Meth. Enzymol. (1978) 48: 380–415.

Immunoassays are generally described in: Collins, Alternative Immunoassays (John Wiley 1985); Freytag, "The Future of Immunodiagnostics," J. Clin. Immunoassay (1991) 14: 239–244 and Gosling, "A Decade of Development in Immunoassay Methodology," Clin. Chem. (1990) 36: 1408–1427.

SUMMARY OF THE INVENTION

Devices for use in analyte detection assays are provided. The subject devices comprise at least one assay path, wherein each assay path includes a main flow path and at least one side reagent channel. The main flow path begins at a sample addition port, continues through a main reagent area into an incubation area and ends in a waste area. In fluid communication with the main flow path is at least one side reagent channel. The side reagent channel begins at a liquid addition port, continues through a side reagent area and is in fluid communication with the main flow path at a region between the main reagent and waste areas, preferably at a region upstream from the incubation area. The assay path is conveniently located in a housing comprising a top and bottom plate, where an optically clear window is present over the incubation area for assay signal detection. Efficient mixing of reagent members in any of the reagent areas and/or in the incubation area may be accomplished by inclusion of agitation means in these areas. Control of reagent member interaction and fluid flow through the device is enhanced through placement of at least one fluid interruption means at a location in the main flow path and/or side reagent channels. The device finds use in a variety of assays, particularly in analyte detection assays where the signal producing system used in the assay is based on interactions between specific binding pair members and an optical signal is related to the presence of analyte in the sample.

DESCRIPTION OF THE SPECIFIC EMBODIMENTS

Figure 1:
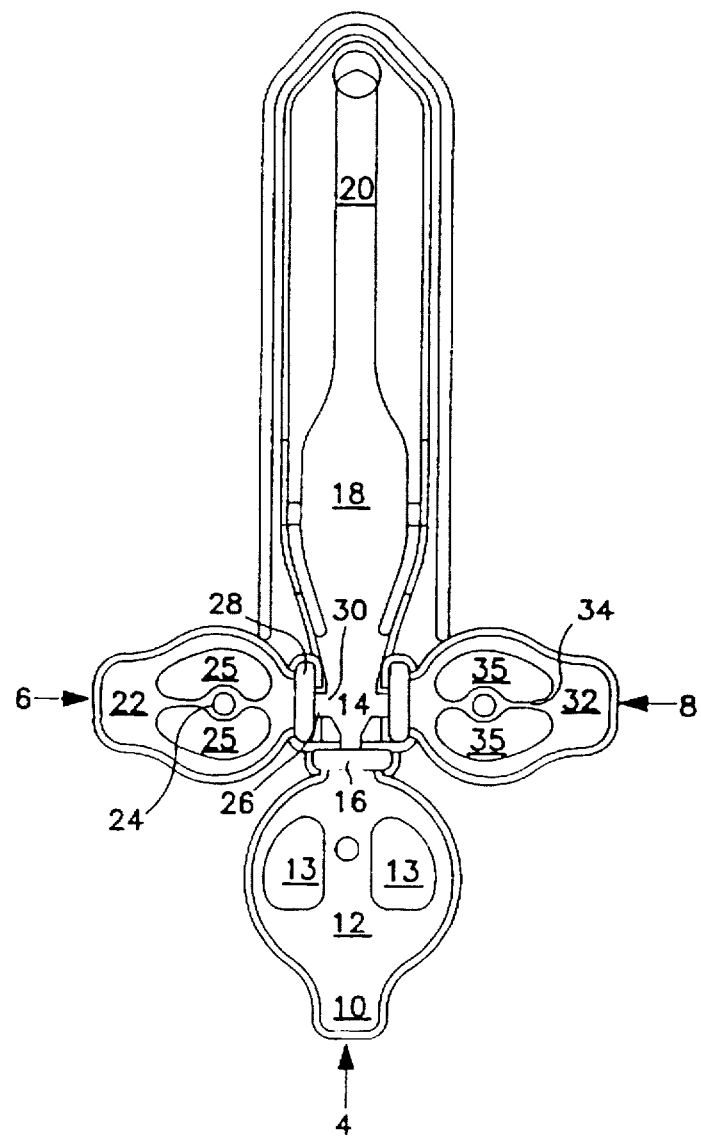
FIG. 1 is an overhead view of an assay path according to the subject invention.

An assay device, and method for its use in the detection of analyte in a sample, is provided. The device includes at least one assay path comprising a main flow path and at least one side reagent channel. The main flow path begins at a sample addition port, continues through a main reagent area into an incubation area and ends in a waste area. Each side reagent channel begins at a liquid addition port, continues through a side reagent area and ends in fluid communication with a region of the main flow path between the main reagent and waste areas, preferably upstream from the incubation area. To provide for homogeneous dispersal of reagents necessary for a particular assay in sample, agitation means may be provided in at least one of the main and side reagent areas and/or the incubation area. Fluid interruption means located at various positions along the main flow path and side reagent channels upstream from the incubation area provide for control of reagent interaction and fluid flow through the device.

The subject device may comprise one or more assay paths, where an assay path includes a main flow path and at least one side reagent channel, usually two side reagent channels. Where the device provides for two assays to be run, i.e. includes two assay paths, the two assay paths can be used for a single assay and a control, for the same assay for two samples, or two different assays for the same or different samples. Thus, various configurations may be employed depending upon the nature of the desired assay. Where two or more assay paths are present in the device, the paths may be in any convenient configuration on the device with respect to each other. Thus, the assay paths may be in parallel relationship, opposing relationship, and the like. Typically, at least a portion of the assay path will be a capillary, wherein by capillary is meant that the dimensions of the main flow path provide for capillary flow of fluid through the flow path or channel. To provide for capillary flow, the height of the flow path in the region of capillary flow will typically range from 0.02 to 2.5 mm, and will usually range from about 0.1 to 0.5 mm.

The main flow path or channel of each assay path commences at a sample addition port. The sample addition port may be any convenient shape for receiving sample into the main flow path, such as square, rectangular, oval or circular, usually circular. The sides of the sample addition port may be cylindrical or beveled, where the diameter of the top of the port is larger than the diameter of the bottom of the port. Where the port is beveled, it may be symmetrically or asymmetrically beveled. The dimensions of the sample addition port will be sufficiently large to receive a volume of sample, where the volume of sample will usually range from 20 to 2000 µL. Where the sample addition port is cylindrical, the diameter of the addition port may range from 0.2 to 1 cm, while where the sample addition port is beveled, the diameter of the top of the sample addition port may range from 0.2 to 1.0 cm, but will typically range from about 0.475 to 0.8 cm, while the diameter of the bottom of the sample addition port may range from 0.1 to 0.4 cm.

Beneath the sample addition port is the sample receiving region. The sample receiving region serves to receive the sample and provide a conduit between the sample addition port and the first reagent area. Preferably, the sample receiving region is sufficiently long to ensure that air outside the device cannot directly access the main reagent area, since air in the reagent area may adversely interfere with the assay being conducted in the device. In some embodiments, the length of the sample receiving region is commensurate with the diameter of the bottom of the sample addition port. The length of the sample receiving region may range from 0.1 to 0.5 cm, usually from 0.5 to 0.3 cm.

The next region in the direction of fluid flow is the main reagent area, which may serve a variety of purposes. First, a member or members of a signal producing system, e.g. dry reagent, may be stored in the main reagent area, so that upon entry of sample into the main reagent area, dry reagent is rehydrated and available for reaction in the assay. Furthermore, the main reagent area may serve as a convenient location for pre-treatment of sample, such as dilution of sample, extraction of sample components by precipitation or the like, and modulation of sample temperature, e.g. raising or lowering of sample temperature, as desired for the particular assay being carried out. Finally, the main reagent area may comprise agitation means, so that the main reagent area serves as a mixing chamber where members of the signal producing system are homogeneously dispersed throughout the sample.

The main reagent area may be any convenient shape, e.g. square, rectangular, oval or circular. Depending on the particular device, a particular shape of reagent chamber may be preferred. For example, where the reagent chamber comprises an impeller agitation means, a circular reagent chamber is preferred. The volume of the reagent area will be sufficient to accept substantially all of the sample or diluted sample volume, in addition to any reagent which may be stored in the reagent area. The distance between the top and bottom walls of the reagent area will be slightly greater than the distance between the top and bottom walls of the main transport conduit and incubation area, described below, ranging from 0.5 to 2.5 mm, usually ranging from 1.0 to 1.5 mm.

Although the reagent in the main reagent area may be present on one or more of the surfaces of the reagent area, preferably the main reagent area may comprise at least one trough, usually two troughs for housing the dry reagent. The troughs may take any convenient shape, where a particular trough's shape will usually be dependent on the overall configuration of the main reagent area, e.g. semi-circular troughs in a circular main reagent area. The depth of the trough floor below the floor of the main reagent area will usually range from about 0.025 to 1.0 mm, more usually from about 0.05 to 0.5 mm.

In fluid communication with, and downstream from, the main reagent area will be at least one incubation area. In some embodiments, the border between the reagent and incubation areas may be so indefinite that the two regions may be considered one region e.g. a reagent incubation area. However, the two regions will typically be separated by a transport conduit. The transport conduit may serve as a conduit for sample from the main reagent area to the incubation area, as well as a variety of additional functions. Depending on the nature of the assay or other protocol being performed in the subject device, the transport conduit may serve as a storage area for various reagents which may be diffusibly or non-diffusibly bound to the walls of the transport conduit. For example, antibodies may be present which serve to remove one or more components from the sample, e.g. cells, interfering components, etc. Chemical reagents may also be located in the main transport channel to change the pH, redox potential or other characteristics of the sample. In this way, sample introduced in the sample port may be modified as necessary for the portion of the assay which is conducted in the incubation area. Finally, the transport conduit may serve as the receiving area, where fluid from the side reagent channel(s) enters, and combines with, the main flow path. Where the transport conduit serves to receive fluid from one or more side reagent channels, the conduit will have at least one inlet port on one of its side walls through which fluid from a side reagent channel may enter. In embodiments where two side reagent channels are present, the conduit will comprise two inlet ports, where the inlet ports will usually be in opposing relationship on opposite sides of the conduit. The distance between the top and bottom walls of the main transport channel will typically range from about 0.02 to 2.5 mm, more usually between about 0.1 and 0.5 mm.

The main flow path opens into the incubation area. In assays where an optical signal is related to the presence and/or amount of analyte in the sample, the incubation area is where the signal which is related to the presence of analyte is produced. On one wall of the incubation area, usually the top wall, will be an optically clear window which provides for viewing of the signal generated by the particular assay being performed in the incubation area. Opposite the top wall is a bottom wall. The bottom wall will be capable of supporting a reagent which may be required for a particular protocol to be carried out in the device. In one embodiment of the device, diffusibly or non-diffusibly bound to the top and/or bottom wall, usually the top wall, may be reagent members of the particular assay to be performed. In an alternative embodiment, the bottom wall will be capable of supporting a reagent but not comprise a reagent. In this embodiment, the user of the device, as necessary, may add reagent to the bottom wall.

In one embodiment, an assay platform may be included which comprises reagent members. The assay platform may simply be an elevated region of a wall of the incubation area, e.g. the bottom or top wall. The elevated region of the platform may conveniently be beveled at the point of contact with the wall in order to modulate the kinetics of fluid flow through the incubation area, so that fluid flow is more uniform across the surface of the assay platform. Alternatively, the assay platform may be a filter which comprises reagent members, e.g. specific binding pair members. The assay platform filter may be attached to the walls of the incubation area so that fluid flowing through the incubation area must also flow through the filter. For example, the filter may be attached to the top and bottom walls of the incubation area, where the points of attachment may be beveled. This embodiment is especially useful in the assay of larger sample volumes or sample volumes in which analyte is present in small amounts.

A plurality of incubation areas may be included in the main flow path, where fluid flows from one incubation area to another sequentially. Where the main flow path comprises a plurality of incubation areas, one may perform different assays in each of the incubation areas on the same sample. The incubation area may range in length from 1 to 3 cm, and usually ranges in length from 1.25 to 2.5 cm, more usually 1.5 to 2 cm. The volume of the incubation area may range from 5 to 200 µl, more usually 20 to 100 µl and will preferably range from 40 to 80 µl.

Located to one side of the incubation area, usually at the far side opposite the side adjacent the transport conduit, will be the waste area. The waste area serves to receive the unreacted sample and/or various wash fluids which flow through the incubation area during a particular assay. The dimensions of the waste area will not necessarily provide for capillary flow. The width of the waste area may be the same as the width of the incubation area, or may taper significantly thereby forming a narrow channel, where the width of the waste area will range from 0.3 to 2.5 cm. The depth of the waste area will range from 0.002 to 0.65 cm. The length of the waste area will range from 0.6 to 2.5 cm.

The waste area may conveniently comprise a vent which serves to release air and other gasses as fluid enters the waste area. Fluid from the waste area may be removed from the device periodically by external means. For example, the vent may also serve as an interface with an external suction means, e.g. a pump. A separation means for separating sample components may be positioned in the flow path downstream from the incubation area and prior to the waste area vent. For example, a filter may be positioned in the waste area prior to the vent so that in assays of samples comprising red blood cells, the red blood cells are retained in the waste area while serum flows through the filter and out the vent. This embodiment is convenient where one uses the device in conjunction with a machine which removes fluid from the flow path through the waste area vent, where one wishes to limit the number of red blood cells which are exported through the waste area vent. The waste area may comprise various means for enhancing fluid flow through the flow paths of the device. Such means may include an absorptive membrane which absorbs liquid from the incubation area. Alternatively, one may provide for a wicking means for removing liquid which has entered the waste area, thereby increasing the volume available for occupation by additional liquid from the device.

In a preferred embodiment of the device, the waste area will be a narrow channel ranging in width from 1.0 to 8.0 mm and ranging in length from 0.5 to 4.0 cm. In this embodiment, the incubation area, which will be wider, will gradually narrow into the waste area.

In a preferred embodiment, in fluid receiving relationship with the incubation and waste areas is an overflow trough for collecting excess fluid, air and other gases from the incubation and waste areas. Downward sloping ramps lead from the floor of the incubation area to the trough, which may have a depth ranging from about 0.025 to 1.27 mm below of the floor of the incubation area, usually from 0.025 to 0.50 mm below the floor of the incubation/waste area. In a preferred embodiment, the trough may be bi-level, with a first level ranging from about 0.025 to 0.10 mm below the floor of the incubation/waste area and the second level ranging in depth from about 0.150 to 0.50 mm below the floor of the incubation area, where the first level is in fluid communication with the second level via a downward sloping ramp. The width of the trough may vary depending on its location in relation to the incubation and waste areas, where the width of the trough will range from 0.08 to 1.0 mm when adjacent to the incubation area and 0.05 to 7.0 mm when adjacent to the waste area. The trough may terminate at the end of the waste area, preferably at the waste area vent.

In addition to the main flow path, the subject device will also comprise at least one side reagent channel or flow path, and more usually will comprise two side reagent channels. Side reagent channels provide for the sequential addition of one or more members of reagents into the incubation area. Furthermore, the side reagent channels provide alternative means of introducing liquid, e.g. wash fluid, into the incubation area, so that one may avoid contamination with reagent remaining in the main reagent area. The dimensions of the side reagent channel may provide for capillary flow through the channel, where the height of the channel may range from about 0.5 to 2.5 mm.

Analogous to the main flow path, the side reagent channels of the subject device originate at a liquid addition port. As with the sample addition port, the liquid addition port may be cylindrical or beveled, symmetrically or asymmetrically. The dimensions of the liquid addition port will be sufficient to accommodate a drop of liquid having a volume ranging from about 5.0 to 50 μl. Where the liquid addition port is cylindrical, the diameter will range from about 0.2 to 1.0 cm, while where the port is beveled, the diameter to the top of the liquid addition port will typically range from 0.2 to 1 cm while the diameter of the bottom of the liquid addition port will typically range from 0.1 to 0.4 cm.

As with the main flow path, beneath the liquid addition port is a liquid receiving region which serves as a conduit for liquid from the addition port to a side reagent area. Preferably, the liquid receiving region is of sufficient length so as to preclude direct access to air outside the device to the side reagent area, where air in the side reagent area may interfere with the assay being conducted in the device. As with the main reagent area described above, the side reagent area may serve as an area where members of the signal producing system are stored, as an area for sample dilution and/or component extraction, as an area where the temperature of the liquid may be modulated and as an area for homogeneously dispersing reagent throughout the liquid. The side reagent area is similar to the main reagent area and may comprise agitation means for mixing reagent with fluid. Furthermore, as with the main reagent channel, troughs may be present in the side reagent area for housing the reagent. The side reagent area will be large enough to accommodate the liquid introduced into the side reagent pathway, as well as any reagent stored in the area or agitation means present in the area, where the volume of the area will usually range from 50 to 150 μl, more usually from 65-70 μl.

Connecting the side reagent area with the main flow path in fluid communication at a region of the main channel between the main reagent and waste areas, e.g. at the incubation area or main transport channel, is a side reagent transport channel. The side reagent transport channel serves as a conduit for liquid, and any reagent member present therein, from the side reagent area to the main channel.

The device will comprise at least one fluid interruption means positioned along the main flow path or the side channels, where the fluid interruption means provides for control over reagent interaction and fluid flow through the device. Usually, the fluid interruption means will be positioned along the main flow paths and/or side reagent channels at a region upstream from the incubation area. The fluid interruption means, in conjunction with the other elements of the device, provides for the subject assays where one need only introduce sample, as well as addition buffer as necessary, into the device and then read the result, no other steps, such as introduction of reagent at a later time, being necessary to perform the assay. The fluid interruption means may be embodied in a variety of ways. Where the device comprises more than one fluid interruption means, the device may comprise one or more types of fluid interruption means.

One type of fluid interruption means comprises a hydrophobic area positioned along the main flow path or side reagent areas, where the hydrophobic area serves to impede fluid flow over the area. Additional fluid interruption means include removable physical barriers to fluid flow. Removable physical barriers of interest include barriers that can be removed by magnetic forces, barriers that dissolve upon contact with fluid, e.g. soluble plugs of polyethylene glycol, and the like.

A preferred fluid interruption means comprises a capillary valve. Capillary valves, as present in the subject devices, may comprise a control capillary that intersects the flow path down which the control of fluid flow is desired. Although the control capillary may intersect the flow path at any convenient angle, the angle of intersection will typically be a right angle. The angle of descent from the floor of the flow path to the floor of the control capillary will be fairly steep, being at least 60°, preferably 90°. Analogously, the angle of ascent from the roof of the flow path to the upper wall of the capillary valve may be at least 60°, and will preferably be about 90°. In an alternative embodiment, the capillary valve is simply a depression in the flow path which is sufficiently deep to impede forward fluid flow across the depression. Typically, the angle of descent into the depression will be greater than about 60°, and will more usually be about 90°. At least one of the floor or roof of the capillary valve, usually the roof, will be hydrophobic.

The capillary valve provides for control over the flow of fluid through the device by disrupting the flow path in which it is employed. Thus, in using the capillary valve, one may control flow in the intersected flow path by emptying or filling the control capillary as appropriate. Alternatively, fluid may be forced through the capillary valved by subjecting the device to sharp, directed motions, which may be caused by the application of external force to the device. In yet another embodiment, fluid flow across the capillary valve may result from the placement of a pressure differential across the valve. This pressure differential may result from an increase in fluid pressure upstream from the valve, e.g. the addition of fluid, or a decrease in fluid pressure downstream from the valve, e.g. by removing fluid from the flow path. In a preferred embodiment where an agitation means is present in the region of the flow path upstream from the capillary valve, fluid flow across the capillary valve is resumed by increasing the magnitude of agitation so that fluid flows across the valve.

To assist in homogeneous dispersal of the various reagents of a particular assay or protocol in the sample and other liquid mediums flowing through the device, an agitation means may be provided in at least one of the main and side reagent areas and/or the incubation area. The agitation means serves to provide sufficient fluid flow so that dry reagent present in the vicinity of the agitation means is efficiently hydrated and homogeneously distributed throughout the fluid. Agitation means includes airflow, shaking, ultrasonic techniques, suction techniques, e.g. where reagent is dehydrated onto a porous membrane and fluid is sucked through the membrane resulting in hydrated reagent, and mechanical means, preferably mechanical mixing means. Suitable mechanical mixing means include mixing means fabricated from magnetic and paramagnetic materials, and may take diverse forms, including propellers, pins, dumbbells, balls, wires, perforated sheets, discs with fins and the like. In a preferred embodiment, the agitation means is an impeller device. Where the material from which the mixing means is fabricated is magnetic or paramagnetic, agitation is conveniently accomplished by applying a moving magnetic field above or below the device, or alternatively, by moving the device through a stationary magnetic field. The rate and/or timing of mixing may controlled as needed to cause the desired level of agitation.

In order to prevent the formation of air pockets in the main flow path or side reagent channels, the device may further comprise air channels. The air channels may be positioned on the top or bottom wall of the flow path or channel, but will usually be positioned on the top path. The air channels may be positioned in any convenient region of the device, such as the main reagent area, the side reagent area, the incubation area, the reference region, as described below, and the like, but will usually be positioned in the main reagent and side reagent areas. For example the air channels may be positioned along the perimeter of the reagent troughs in the main reagent area. The air channels may be any convenient shape, where the air channels may range in depth from 0.025 to 1.27 mm. The length of the air channels will vary depending on the location of the air channel in the device, and may run the entire of length of the region in which it is positioned, e.g. the entire length of the main reagent area, or run for only a portion of the length of the region of the device in which it is positioned.

In order to enhance the flow of fluid through various regions of the device, the device may also comprise hydrophilic regions positioned along the main flow path and/or side reagent channels.

The device may be varied as to size, usually being at least about 1 cm×1 cm and not more than about 20 cm×20 cm, preferably having a shorter dimension in the range of about 4–7 cm and in a longer direction by about 5–10 cm. While for the most part, the device may be any convenient shape, generally, it will be rectangular where the edges may be modified by rounding, cutting the corner(s), or other modification which will allow for easy handling and adapting the device to an instrument with which it is used. The thickness of the device will generally vary from about 1 mm to 3 cm, more usually from about 1.5 mm to 4.0 mm.

Also included in the device may be a reference region which serves to provide an indication of the operability of the members of the signal producing system being employed, where the reference region may comprise reagent troughs and agitation means analogous to the main and side reagent areas of a flow path. For example, where a signal producing system comprises enzyme and substrate, where the substrate is converted to a detectable product, the reference zone may comprise dehydrated enzyme and substrate. When the device is used, a drop of fluid is placed in the reference zone. Appearance of enzyme product indicates the enzyme is active, thus indicating that the enzyme in the device will be operative. The reference region will be positioned in the device at a region which is not in fluid communication with the assay path(s) of the device, so as not to interfere with an assay being conducted with the device.

Conveniently, when the device is used in conjunction with an automated instrument, the disposable device may comprise an additional trough for receiving priming fluid used to prime conduits in the instrument prior to running the actual analyte assay procedure. The additional priming trough will be located on the device at a region which is not in fluid communication with the assay path(s) present in the device. Finally, for purposes of device and sample identification, a bar code may be placed in one area of the top or bottom plate.

The assay paths comprising the main flow path(s) and side reagent channels of the cartridge will be in a housing, where the housing will usually be made of two plates, which will be sealed together. Conveniently, one plate will serve primarily as a cover and provide the various ports and optical window(s), while the other plate will provide the various structures necessary for the reservoirs and channels associated with the device. Therefore, the plate into which the majority of the various reservoirs and channels are molded, e.g. the bottom plate, will usually be thicker than the cover plate, e.g. the top plate, generally about 1.5–2-fold thicker than the cover plate.

The plates may be molded out of various plastics which allow for reasonably accurate tolerances, can withstand the various chemicals involved, and will allow for the presence of an optically-clear area. Materials of interest include glasses and plastics. Plastics which fulfill these requirements include acrylate, polystyrene, e.g. Dow 666 polystyrene, polycarbonate, SAN, ABS, etc. Materials can be treated to provide for better wetting characteristics, flow and biological receptor adherence. Methods of treating the plates may include protein binding, gamma irradiations, plasma etching, sugar coating, surface texture modification, e.g. roughening the surface, and the like.

On the top or bottom plate, usually the bottom plate, may be included a sealing means which provides for a sufficiently complete seal between the top and bottom plates during the assembly of the device. This sealing means may take the form of projections spaced along the outside of the channels that project above the top surface of the plate or a raised ridge tracing the perimeter of at least one of the assays paths, references regions and priming trough, usually extending 0.07 mm to 0.7 mm above the top surface of the plate. This projections or ridge is typically fabricated from the same material as the top and bottom plates of the device and upon assembly of the device, as further described below, the projections or ridge may be melted by ultrasonic techniques or other suitable means to make a seal between the top and bottom plates.

In some embodiments, for convenience in introduction of reagents into the device a moat may be included in the bottom plate of the device which surrounds the perimeter of the overflow trough. The depth of the moat may range from 0.05 to 1.0 mm and the width of the mote may range from 0.1 to 1.5 mm.

To assemble the device, the appropriate reagents may be placed at their proper sites, e.g. coating the surface of the troughs in the reagent areas. The necessary members of the signal producing system. e.g. binding pair members, lipid layers, fluorescence production layers and the like, are positioned on the assay platform using conventional means. After the reagents have been positioned, the top housing can be placed in registry over the bottom housing and the edges sealed by any appropriate means, such as ultrasonic welding, adhesives, gasket seals etc. The device is then ready to be stored for subsequent use. Although the device is described above in terms of a device which comprises reagent members of a signal producing system, also encompassed within the subject invention are devices which do not comprise reagent members of a signal producing system. In these devices, a user will first introduce reagent into the proper region of the device, e.g. the side reagent area, and then use the device in an assay, as desired.

The device having been described, applications in which the subject device may find use will now be discussed in greater detail. A wide variety of applications may be carried out in the subject device, where suitable applications will involve the interaction of a sample with reagent members. Illustrative applications include assays where the signal producing system is based on interactions between specific binding pair members and an optical signal is generated by the system which is related to the presence of analyte in the assayed sample.

In carrying out such an assay in the device, one may assay any type of liquid, where the liquid may be assayed directly or may be subjected to prior treatment, depending upon the nature of the liquid and the analyte of interest. The liquid may contain a sample or be a sample from any source, such as a physiological source, e.g. blood, serum, plasma, urine, saliva, spinal fluid, lysate, nasal pharyngeal aspirates etc.; sample of ecological interest, e.g. water, soil, waste streams, organisms, etc.; food, e.g. meat, dairy products, plant products, other organic matter etc.; drugs or drug contaminants in processing; or the like.

The analyte may be any compound which can be detected and is a member of a specific binding pair, either ligand or receptor. The term "receptor" is used arbitrarily, since its origin had to do with surface membrane proteins, where the compound which bound to the surface membrane protein was referred to as a ligand. Receptors include naturally occurring receptors, e.g. enzymes, lectins, surface membrane proteins, antibodies, recombinant proteins, etc., synthetic receptors, nucleic acids, c-glycosides, carbohydrates, gangliosides, chelating compounds, etc.

For the purpose of the subject invention, it is sufficient that two molecules have a significant affinity for each other, where the binding constant will usually be at least about $10^5$ mol$^{-1}$ and one may choose to refer to either member as the receptor. Compounds of interest have to some degree been indicated by indicating the various sample sources. The analyte may be any type of compound, e.g. small organic molecules, peptides and proteins, sugars, nucleic acids, complex carbohydrates, viruses, bacteria particles, lipids and combinations thereof, naturally occurring or synthetic or combinations thereof, so long as there is a complementary binding member. The analytes will frequently include drugs, both naturally-occurring and synthetic, various components of animals, including humans, such as blood components, tissue components, and the like; microorganisms, such as bacteria, fungi, protista, viruses, and the like; components of waste streams or products or contaminants of such products in commercial processing; components in the environment, particularly contaminants, such as pesticides, microorganisms, and the like.

Depending upon the nature of the sample, the sample may be subjected to prior treatment, such as extraction, distillation, chromatography, gel electrophoresis, dialysis, dissolution, centrifugation, filtration, cell separation, and the like. For blood, one may wish to remove red blood cells to provide plasma or serum but their removal is not necessary. Various media may be employed, which will allow for providing for a sample solution or dispersion which can be used in the subject device.

After appropriate pretreatment, if any, the sample in liquid form is then introduced into the sample port. The volume of sample may range from about 1 µl to about 0.5 ml, more usually from about 10 µl to 250 µl, preferably from about 25 µl to 170 µl. The sample is drawn from the sample receiving region beneath the sample application port by capillary action into the main reagent area. In the main reagent area, the sample may combine with a member of a signal producing system, be diluted, components may be extracted from the sample, and the like. If the main reagent area comprises agitation means, the sample may be agitated, thereby hydrating any dry signal producing system member present in the main reagent area and dispersing the hydrated member homogeneously throughout the sample. Depending on the particular signal producing system, a variety of members may be included in the main reagent area, including antibodies or fragments thereof, antibody/enzyme conjugates, antibodies labeled with a dye molecule, specific for analyte or binding member in the incubation area, chemiluminescent labels, and the like.

The sample flows from the main reagent area into the main flow path. Where the main reagent area and the main transport channel are separated by a capillary valve, the capillary valve may be filled to provide for fluid flow into the main transport channel. Further, the vigor of agitation in the main reagent area may be increased to provide the necessary force to move sample into the transport channel. As the sample proceeds down the main flow path, it dissolves and/or reacts with any reagent which may be present in the transport conduit.

As the sample flows into the incubation area, the presence of sample may be detected through the optical window in the incubation area, thereby allowing one to monitor fluid flow through the area. In the incubation area, the sample may combine with other members of the signal producing system which may be present in the incubation area. Other members of the signal producing system which may be present in the incubation area may be members of specific binding pairs, fluorescent production layers as described in U.S. application Ser. No. 08/089,975, filed Jul. 9, 1993, the disclosure of which is incorporated herein by reference and lipid layers as described in U.S. Pat. Nos. 5,156,810 and 5,268,305, the disclosures of which are incorporated by reference.

Instead of having reagent members of the signal producing system distributed in various locations of the assay device, a homogenous assay can be performed in the subject devices, where all of the reagent members of the signal producing system are combined with the sample prior to entering the incubation area. For example, where the reagents members of the signal producing system include dried microparticles, the sample and reagent members may be combined and allowed to react to completion in the reagent are and then moved into the incubation area. The requisite control of fluid flow is provided by the fluid interruption means.

Signal production systems which find use in the application may involve competition or cooperation. In the case of competition, the conjugate will bind to either the analyte or binding sites in the incubation area, e.g. on the walls of the incubation area, on an assay platform in the incubation area, on a membrane in the incubation area, and the like. By having a limited number of conjugate molecules, the number of conjugate molecules which can bind to the complementary binding member will be inversely proportional to the number of molecules of analyte in the sample. Thus, the number of labels which ultimately become bound in the incubation area will be inversely proportional to the number of analyte molecules in the sample. This approach will normally be employed with small analytes, particularly haptenic analytes, where the analyte can only bind to a single receptor.

By contrast, with larger analytes, which are polyepitopic, one has the opportunity for two receptors to bind simultaneously. In this way, the analyte may serve as a bridge between the complementary binding member bound to the membrane and the complementary binding member which is labeled. One may also use the competitive protocol, by having the specific binding pair member of the conjugate capable of competing with the analyte for binding to the bound binding member.

Where a member of the signal producing system is a membrane in the incubation area, the membrane may be divided up into a plurality of sections, where each section may have the same or different specific binding pair member. In this way, the sample may be assayed simultaneously for a number of different analytes. Depending upon the nature of the different analytes, the same or different members of the signal producing system, e.g. conjugates, would be present in the incubation area. The assay could be carried out in the same way, except at the time of reading, one would specifically address different regions of the membrane to identify the signal coming from each of the individual regions. Instead of having a single membrane divided into a plurality of regions, a plurality of membrane spots may be cast onto a wall of the incubation area, wherein each membrane spot comprises a different specific binding pair member. Membrane spots may be cast onto a wall of the incubation area using any convenient means. Preferably, the wall of the incubation area will be hydrophobic so that the membrane spots, once cast onto the wall, do not spread across the surface and thereby merge with other spots. In these embodiments where a plurality of membrane regions are provided, either by having different regions of a continuous membrane or a plurality of membrane spots, preferred label members will be non-diffusible, such a fluorescent labels or enzymes which convert substrates to non-diffusible dyes. These embodiments provide for the possibility of panel testing, such as may be useful in cardiovascular heart disease diagnosis, allergy diagnosis, viral infection diagnosis, fertility diagnosis, and the like.

After sufficient time for substantially complete reaction of the analyte in the incubation area, the incubation area may be washed to remove substantially all of the sample and unreacted members of the signal producing system. A buffered aqueous solution may be used which is appropriate for maintaining the binding of the specific binding pair members. Buffer may be introduced through the main sample addition port or one of the side reagent ports, where the buffer travels down the main or side reagent channels respectively and into the incubation area. Usually, the volume of the wash solution will be at least about equal to the volume of the sample and may be 40-fold more or greater than the volume of sample, and preferably at least about 2-fold greater than the volume of sample. Washing of the incubation area may be enhanced with agitation, where agitation means are included in the incubation area.

Depending upon the signal producing system employed, it may be necessary to introduce an additional member or members of the signal producing system into the incubation area after the sample has been introduced. To introduce the additional member or members (which may be stored in the side reagent area) liquid, e.g. buffer, is introduced into the liquid addition port, whereby it flows into the side reagent area. In the side reagent area, the additional member will combine with the liquid and be carried into the incubation area, where it may participate in the signal producing system. For example, where an enzyme is the label used in the signal producing system, the enzyme or enzyme conjugate may be contained within the side reagent area. It will be necessary to provide substrate to obtain a detectable product, where the detectable product is either directly detectable or acts to modulate the signal of another member of the signal producing system, e.g. binding pair members, a fluorescent production layer, a fluorescent lipid membrane. One of the side reagent areas could house this substrate. Upon addition of buffer to the liquid addition port, the substrate is hydrated and then flows into the main flow path, where it is converted by the enzyme in the incubation area to a detectable product. Alternatively, where the label is a chemiluminescent label, members which may be introduced into the incubation area via the side reagent channels will include reagents necessary for reacting with the label to provide the luminescent signal. In another signal producing system which may find use in the subject device, additional members may be reagents which directly or indirectly modulate the fluorescence of a fluorescent lipid membrane in the incubation area. Direct modulation may result from binding events, where the binding events change the conformation of the lipid layer thereby changing its optical properties. Indirect modulation may result from binding events which change the environment of the lipid layer, e.g the pH, temperature, mechanical stress, ionic strength and the like. Optical properties which may be directly or indirectly modulated in response to the presence of analyte include changes in the emission or absorption characteristics of the lipid layer. Alternatively, where diffraction particles are the detectable label, as described in co-pending application Ser. No. 08/326,978 filed Oct. 21, 1994, the diffraction particles may be stored in the dry reagent area and upon hydration, flow into the incubation area and participate in the assay, where participation may comprise binding to specific binding pair member on the platform or agglutinating in the incubation area in a manner which is dependent upon the amount of analyte present in the area. Introduction of the additional member or members into the incubation area may be followed by additional washings to again remove unreacted members of the signal producing system, as needed.

The final step in using the subject device in an assay is to read the detectable signal. The detectable signal is read through the optically clear window located opposite the assay platform. Reading the detectable signal may comprise a single measurement or series of measurements, e.g. to determine a rate or to wait for background signal to fade, depending on the assay. Further, one may read the signal generated and compare it to the signal read from a control, where the control comprises a predetermined amount of analyte, including no analyte. Depending upon the signal producing system, it may be necessary to irradiate the incubation area so as to obtain a detectable signal, e.g. where a fluorescent label is employed.

The structural configuration of the subject device provides the opportunity to run a wide variety of assays using diverse signal producing systems. Although partially indicated previously, labels which may be employed are those that provide an optical signal and include fluorescent and chemiluminescent labels, enzymes which convert substrate to detectable product, particles for aggregation and diffraction assays, dye molecules attached to antibodies, and the like. Optical signals which may be detected through the optically clear window and related to the presence and/or amount of analyte in the sample include emissions, e.g. from fluorescent and chemiluminescent labels, fluorescence quenching of a member of the signal producing system, light scattering and diffraction, such as that associated with aggregation systems or diffraction particles, e.g. agglutination of red blood cells, changes in refractive index, e.g. plasmon resonance, changes in absorption or transmittance, e.g. color changes of polydiacetylene layers from blue to red, modulation of linear and circular birefringence and/or dichroism of a polydiacetylene film, fluorescent enhancement of polydiacetylene films, and the like.

In addition to assays based on the interaction of specific binding pair members, one may also employ the subject device in simple chemical assays, where the interaction of signal producing system members in the presence of analyte results in a detectable signal, which may be observed through the optical window of the device. Such assays may include assays for glucose, cholesterol, triglycerides and the like. For example, in a glucose assay, a blood sample may be combined with reagents which produce a color in the presence of glucose, where the color signal may be viewed through optical window.

Additional applications in which the subject device may find use include nucleic acid amplification protocols, such as those based on polymerase chain reaction (PCR) as described in Sambrook. Fritsch & Maniatis, Molecular Cloning-A Laboratory Manual (Cold Spring Harbor Laboratory Press, 1989) and ligase chain reaction (LCR) as described in Laffler et al., "The Ligase Chain Reaction in DNA-Based Diagnosis," Ann. Biol. Clin. (1993) 51: 821–826. The subject device may also be used in conjunction with biosensors which provide for mass detection methods, such as those described in Tailor, R. F., Biosensor Technology Applications and Market Analysis (Burlington Mass.; Decision Resources) and Turner, Karube and Wilson, Biosensors: Fundamentals & Applications (Oxford University Press) 1987.

Other applications of interest in which the subject device may find use include whole blood assays involving optical diffraction, in synthetic organic or biochemical reactions, in assays using magnetic particles, in cell preparation applications, culturing applications, and the like.

The various applications of the fluid to the disposable device required in a particular application can be conveniently carried out automatically with an appropriate instrument. Thus, the instrument may measure the sample and wash volumes introduced into the device, time the incubations, maintain constant temperature, and take the reading, as appropriate.

The device will now be further described in terms of the figures. In FIG. 1 is depicted a representational view of an assay path 2 with a main flow path 4 and two side reagent channels, 6 & 8. The main flow path begins at the sample receiving region directly below the sample addition port 10. In fluid communication with sample receiving region 10 is main reagent area 12. The reagent area may comprise troughs for storing the reagent 13. Main reagent area 12 is separated from flow path 14 by capillary valve 16. Fluid in the main transport channel 14 flows into incubation area 18. The incubation area may house an assay platform (not shown), where at least a portion of the steps of the application being conducted may occur. Adjacent to the incubation area is a waste area 20. The waste area 20 ends at outlet port (not shown). Side reagent channel 6 begins in liquid receiving region 22 which is directly below the liquid addition port (not shown). In fluid communication with region 22 is side reagent area 24, which comprises side reagent troughs 25. Separating side reagent reservoir 24 from side transport channel 26 is capillary valve 28. Side transport channel 26 opens into main transport channel 14 at entrance 30. Second side reagent channel 8 comprises, in the direction of fluid flow, second liquid receiving region 32 and second side reagent area 34 comprising reagent troughs 35.

Figure 2:
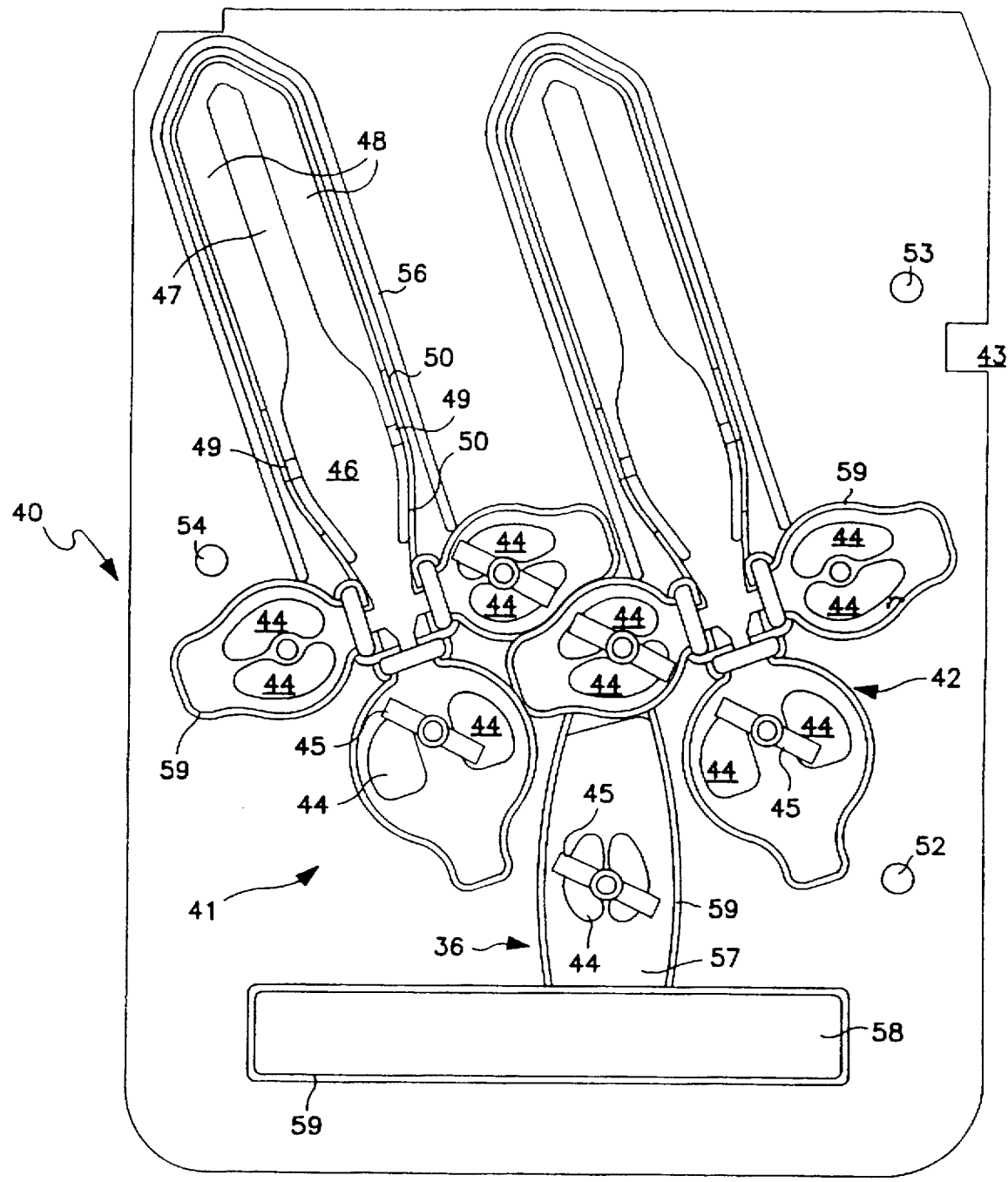
FIG. 2 is an overhead view of the bottom plate of a device in accordance with a preferred embodiment of the subject invention, where the incubation area narrows into a long, channel-like area and the main and side reagent areas comprise reagent troughs and agitation means.

In FIG. 2 is depicted a 2-dimensional, overhead view of a bottom plate 40 of a preferred embodiment of the subject device. Bottom plate 40 shows one possible configuration comprising adjacent assay pathways 41 and 42. The sides of plate 40 comprise notch 43 for aligning and securing the device with an instrument, where the device is employed with an instrument. (See FIG. 3). In addition to assay pathways 41 & 42 are reference zone 36, comprising a liquid receiving region 57, and priming trough 58. In the main and side reagent areas, as well as the in the reference zone, are troughs 44 for holding reagent and impellers 45 for agitation. The incubation area 46 narrows to waste area 47. On opposite sides of the incubation and waste areas is a bi-level trough 48 which serves to receive overflow liquid from the incubation and waste areas. A ramp 49 joins one level of the trough 48 to the other level. Surrounding the perimeter of the incubation/waste area and trough is a moat 56. Also present are pins 52,53 & 54 for aligning and locking the bottom plate with the top plate and notches 50. Along the perimeter of the assay paths, the priming trough and the reference zone is a slightly raised protrusion 59 which acts as a sealing means during assembly of the device, where the top plate, see FIG. 3, is sealed to the bottom plate 40.

Figure 3:
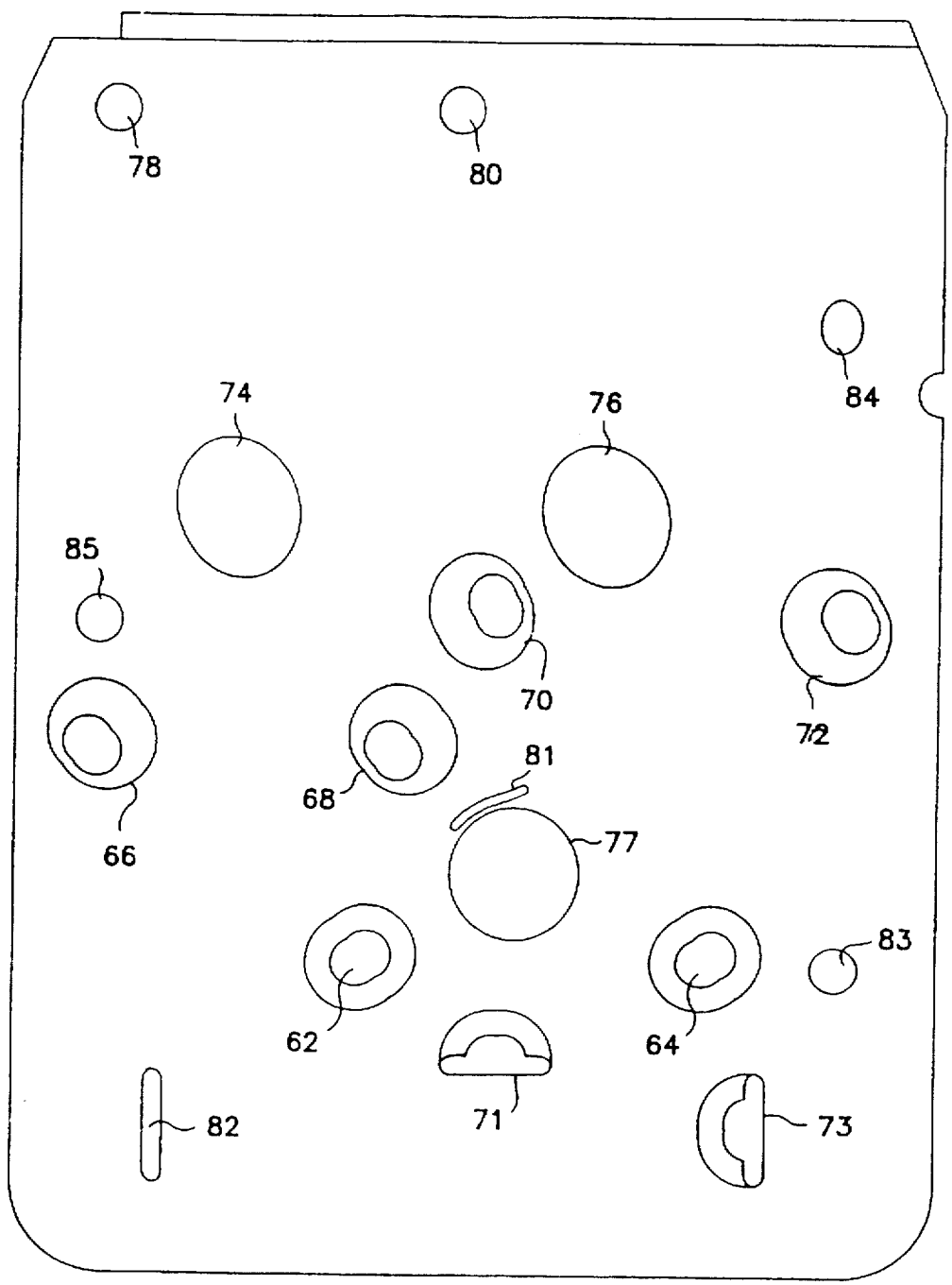
FIG. 3 is an overhead view of the top plate of the device in accordance with the subject invention.

In FIG. 3 is depicted top plate 60 which would correspond to bottom plate 40 of FIG. 2. Top plate 60 comprises sample addition ports 62 and 64 directly above the sample receiving regions of the two main flow paths beneath. Liquid addition ports, 66,68,70 and 72 provide means for introducing liquid into the side reagent pathways below, while port 71 and port 73 provide for the introduction of liquid into the reference zone and priming trough, respectively. Optically clear windows 74 and 76 provide means for viewing the signal generated in the incubation area below, while optically clear window 77 provides for viewing of the reference zone. The optically clear windows may be indented safeguard the window from scratches during manufacture and handling. Air vents 78 and 80 provide outlet means for air and other gases from the waste reservoirs below, while air vents 81 and 82 allow for escape of air and gases from the reference zone and priming trough, respectively. The air vents may also provide for connection with an external suction means for enhancing fluid flow through the device. Detents 83, 84 & 85 provide for alignment with pins 52, 53 & 54 on bottom plate 40.

Figure 4:
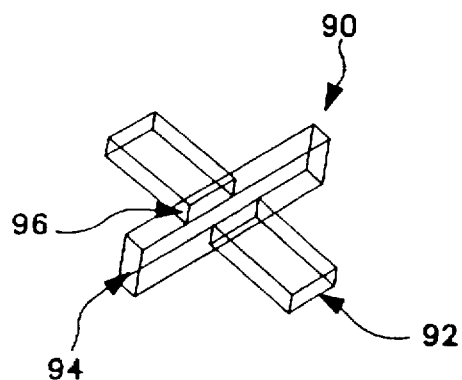
FIG. 4 is a three dimensional view of a capillary valve in accordance with the invention.

In FIG. 4 is depicted a three dimensional view of one embodiment of the capillary valve which may be employed in the subject device. Capillary valve 90 comprises flow path 92 (e.g. main or side reagent flow path) and control capillary 94 at right angles to each other, so that control capillary 94 intersects flow path 92 at intersection 96. This intersection disrupts fluid flow in flow path 92 when control capillary 94 is empty, but does not impede fluid flow through flow path 92 when it is full.

Figure 5:
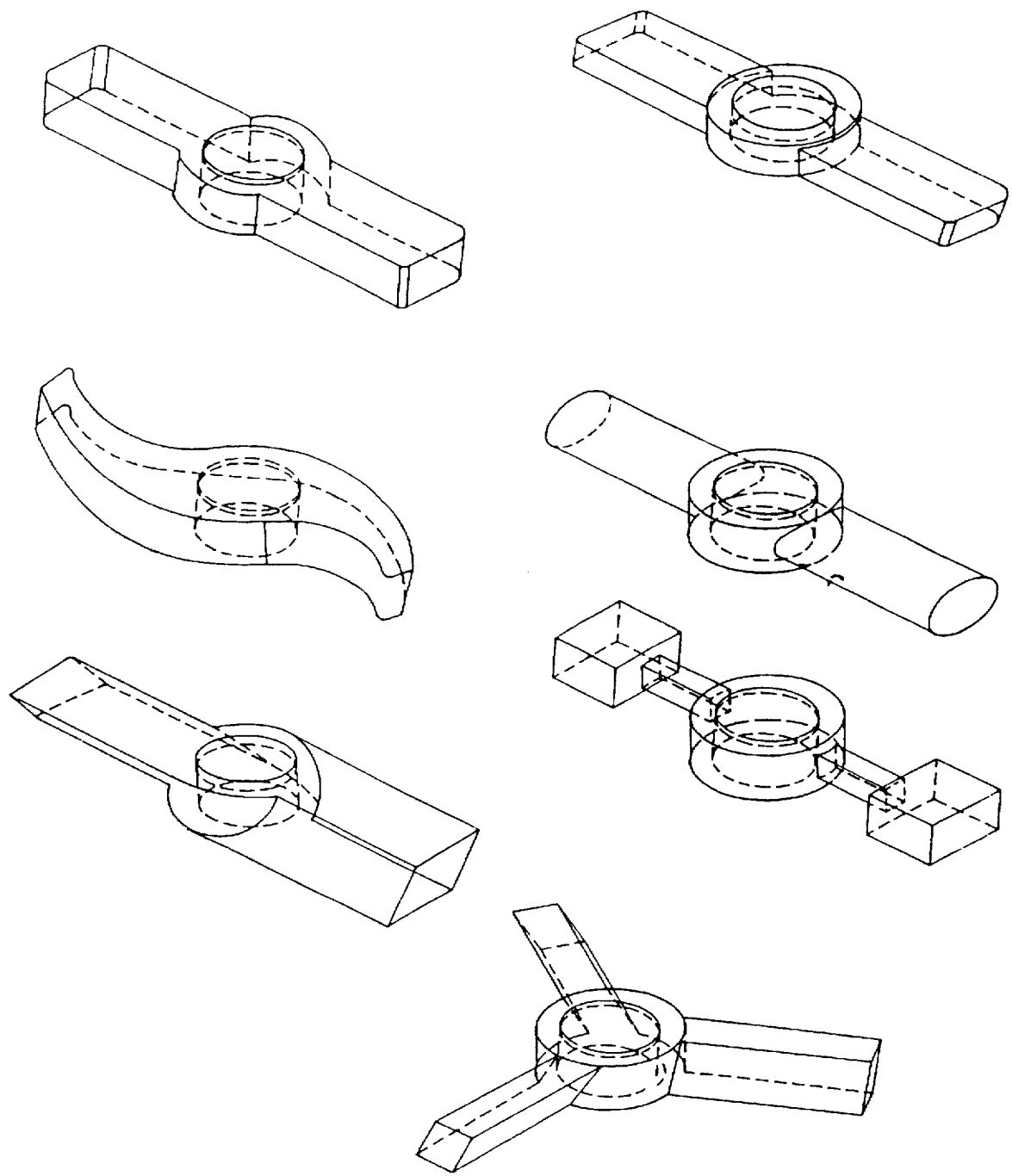
FIG. 5 provides three dimensional representations of various impeller structures in accordance with the subject invention.

In FIG. 5 are several three dimensional views of impeller configurations suitable for use as agitation means in the subject device. In the impeller, the various arm configurations are positioned on a central axis which provides for clockwise and counterclockwise rotation. Thus, when the arm is rotated on the axis, turbulence or agitation is created in its vicinity.

Figure 6:
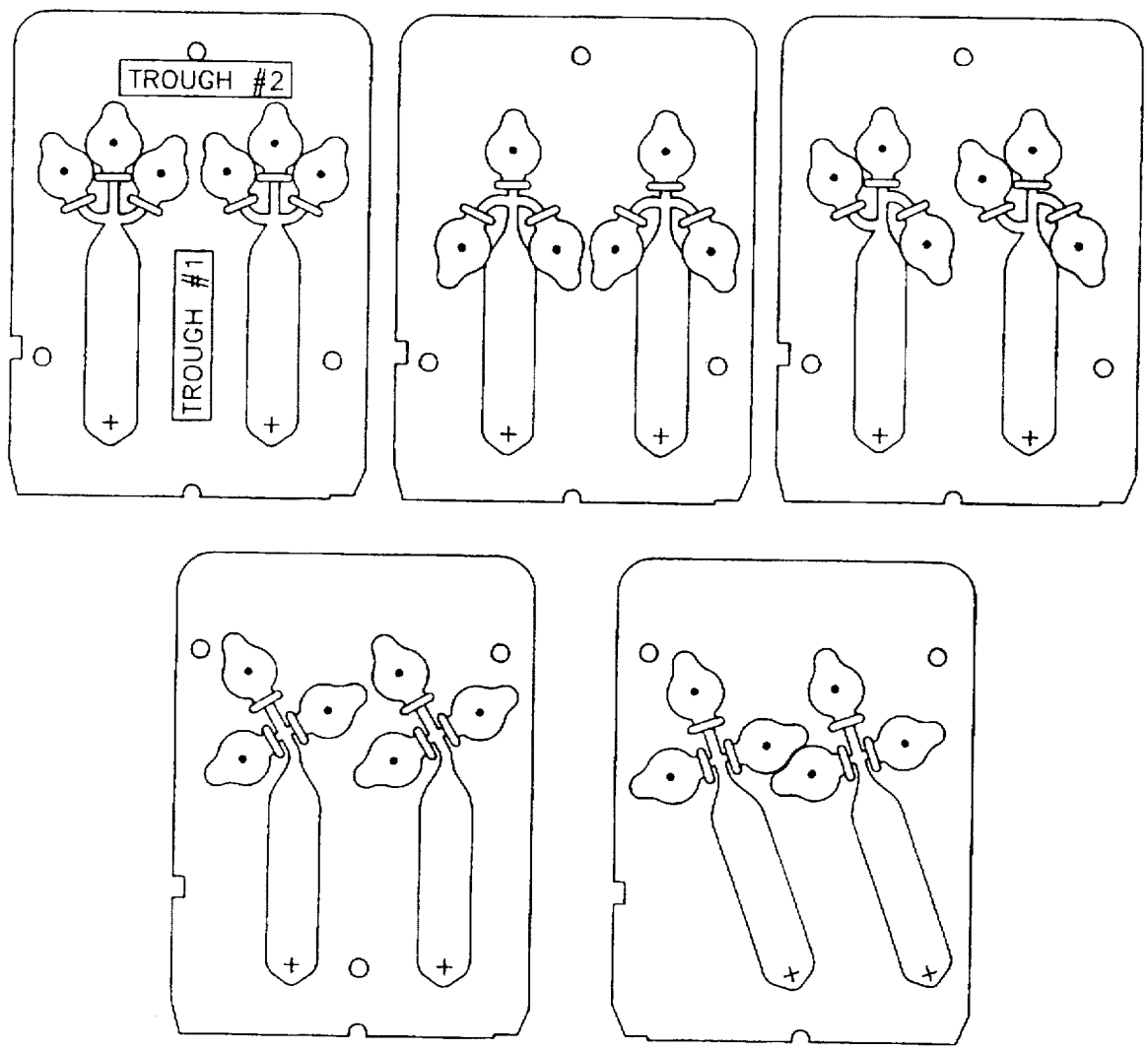
FIG. 6 depicts alternative bottom plate configurations in accordance with the subject invention.

In FIG. 6 are several two dimensional views of various bottom plate configurations, where it is shown that the side reagent flow paths may be positioned in a variety of orientations in relation to the main flow path.

Figure 7:
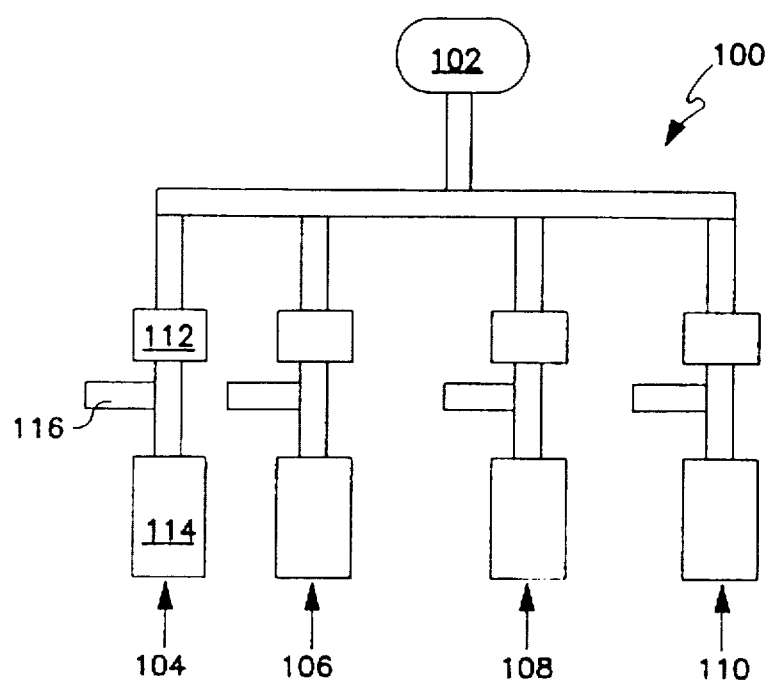
FIG. 7 is an overhead view of an alternative embodiment of an assay path of the subject invention.

FIG. 7 provides a two dimensional top view of the assay path of an alternative embodiment of the subject invention. Assay path 100 originates in sample addition port 102. The sample which enters the sample addition port diverges into a plurality of main channels, 104, 106, 108, 110. Main channel 104 will be described in greater detail, it being representative of the other main channels. Sample first enters main reagent area 112. From main reagent area 112, sample flows into incubation area 114. Side reagent channel 116 allows for introduction of wash fluid or additional reagent into main channel 104.

Figure 8:
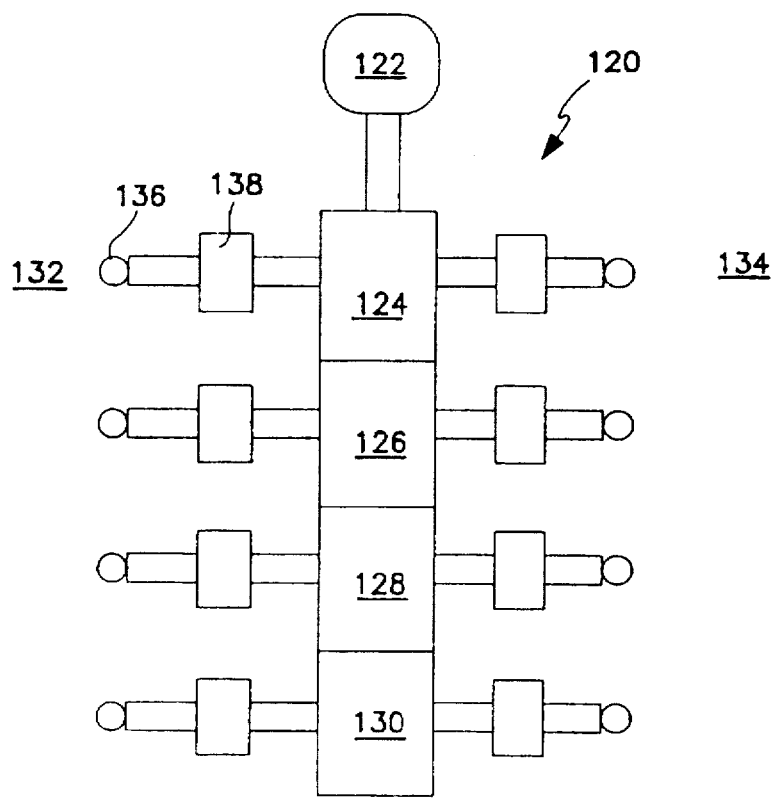
FIG. 8 is an overhead view of an alternative embodiment of an assay path of the subject invention.

FIG. 8 provides a two dimensional, top view of the assay path of another alternative embodiment of the subject invention. Assay path originates in sample addition port 122. Sample flows from sample addition port through a plurality of incubation areas 124, 126, 128 and 130 sequentially. Incubation area 124 will be further described, it being representative of each of the incubation areas. Side reagent channels 132 and 134 are in fluid communication with incubation area 124. Side reagent channel 132 comprises liquid addition port 136 and side reagent area 138.

It is evident from the above discussion that an improved device for use in diagnostic assays is provided. The device provides for improved control over reagent mixing and fluid flow through the device. Further, the device requires minimal operator interaction and is simple to use. Despite the simplicity of use, the device provides for reliable and reproducible results. Finally, the configuration of the device is such that a wide variety of assays which employ diverse signal producing systems to obtain a detectable signal may be employed, providing for increased manufacturing scales and reduced unit cost.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A device for use in analyte detection comprising:
    (a) a main flow path comprising:
        a sample addition port for adding a sample suspected of containing an analyte;
        at least one reagent incubation area downstream from said sample addition port;
    and
        a waste area downstream from said reagent incubation area;
    (b) at least one side channel, said side channel comprising:
        a liquid addition port and
        a side reagent area for introducing a liquid into said reagent incubation area;
    (c) at least one fluid interruption means positioned along said main flow path or side channel upstream from said reagent incubation area; and
    (d) at least one reagent in said main flow path or said side channel,
    wherein said side channel is in fluid communication with said main flow path at a region of said main flow path upstream from said incubation area and wherein said analyte, if present, reacts with a reagent to produce a detectable signal in said reagent incubation area.

2. The device according to claim 1, wherein at least a portion of said main flow path is a capillary.

3. The device according to claim 1, wherein said device further comprises agitation means in at least one of said reagent incubation and side reagent areas.

4. The device according to claim 1, wherein said device comprises a plurality of main flow paths in fluid communication with said sample addition port.

5. The device according to claim 1, wherein said main flow path comprises a plurality of incubation areas.

6. The device according to claim 1, wherein said fluid interruption means is a capillary valve.

7. An assay device for use in analyte detection comprising at least one assay path, wherein said assay path comprises:
    (a) a main flow path comprising
        (i) a sample addition port for adding a sample suspected of containing an analyte;
        (ii) a main reagent area that is adjacent said sample addition port and that contains a reagent;
        (iii) a transport conduit downstream from said main reagent area comprising two inlet ports in opposing relationship;
        (iv) an incubation area downstream from said transport conduit; and
        (v) a waste area downstream from said incubation area;
    (b) two side reagent channels on opposite sides of said main flow path comprising:
        (i) a liquid addition port and
        (ii) a side reagent area, wherein each of said side reagent channels is in fluid communication with said main flow path at a corresponding inlet port at said transport conduit; and
    (c) at least one capillary valve in said main flow path or side reagent channel upstream from said incubation area;
    wherein said analyte, if present, reacts with a reagent to produce a detectable in said incubation area.

8. The device according to claim 7, wherein said incubation area has a volume ranging from 5 µl to 200 µl.

9. The device according to claim 7, wherein said incubation area comprises an assay platform.

10. The device according to claim 9, wherein said assay platform comprises an elevated region of floor of said incubation area.

11. The device according to claim 9, wherein said assay platform comprises a filter.

12. The device according to claim 7, wherein at least a portion of said main flow path is a capillary.

13. The device according to claim 7, wherein said device further comprises an agitation means in at least one of said main and side reagent areas.

14. The device according to claim 7, wherein said device further comprises at least one air channel positioned in at least one of said main flow path and side reagent channels.

15. An assay device for use in analyte detection comprising at least two assay paths, wherein each of said assay paths comprises:

(a) a main flow path comprising:
      (i) a sample addition port for adding a sample suspected of containing analyte;
      (ii) a main reagent area adjacent said sample addition port comprising at least one reagent trough for containing reagent and an agitation means;
      (iii) a transport conduit that is downstream of the main reagent area, upstream of an incubation area and comprises two inlet ports in opposing relationship;
      (iv) an incubation area being downstream of said transport conduit; and
      (v) a waste area that is downstream of said incubation area and that comprises an outlet port;
   (b) two side reagent channels on opposite sides of said main flow path, wherein each of said side channels comprises:
      (i) a liquid addition port; and
      (ii) a side reagent area comprising an agitation means and at least one reagent trough for containing reagent, wherein each of said side reagent channels is in fluid communication with said transport conduit at one of said inlet ports of said transport conduit;
   (c) at least one capillary valve in at least one of said main flow path and side reagent channels upstream from said incubation area; and
   (d) a reagent in the reagent trough of at least one of said main reagent area or said side reagent areas, wherein said analyte, if present, reacts with a reagent to produce a detectable signal in said incubation area.

16. The device according to claim 15, wherein said agitation means is an impeller.

17. The device according to claim 15, wherein said assay paths are present in a housing, said housing comprising a top and bottom plate fastened together, wherein said top plate has an optically clear window for viewing said detectable signal.

18. The device according to claim 17, further comprising a reference region which is not in fluid communication with said assay path.

19. The device according to claim 17, further comprising a priming trough which is not in fluid communication with said assay path.

20. The device of claim 15, further comprising an overflow trough in fluid receiving relationship with said incubation and waste areas.

21. A method for determining the presence of an analyte in a sample using a device having: (a) a main flow path comprising: (i) a sample addition port for adding a sample suspected of containing an analyte; (ii) at least one reagent incubation area downstream from said sample addition port; and (iii) a waste area downstream from said incubation area; (b) at least one side channel comprising (i) a liquid addition port and (ii) a side reagent area, wherein said side channel is in fluid communication with said main flow path upstream of said incubation area; (c) at least one fluid interruption means in one of said main flow path and side channel; and (d) at least one reagent that is a member of a signal producing system and that is in said main flow path or said side channel, wherein said side channel is in fluid communication with said main flow path at a region of said main flow path upstream from said waste area, said method comprising:
   introducing sample suspected of containing an analyte into said sample addition port, whereby said sample flows down said main flow path and reacts with a reagent member of said signal producing system;
   washing said reagent incubation area substantially free of sample components unreacted with a member of said signal producing system;
   introducing liquid comprising at least one additional member of said signal producing system into said incubation area, whereby an optically detectable signal is produced in said incubation area; and
   detecting said optical signal at least one time to determine the presence of analyte in said sample.

22. A method according to claim 21, wherein the signal producing system comprises an enzyme label which converts a substrate to a fluorescent product.

23. A method according to claim 21, wherein the signal producing system comprises a chemiluminescent label.

24. A method according to claim 21, wherein at least one member of the signal producing system comprises an antibody-dye label and wherein said antibody-dye label reacts with said suspected analyte or other member of said signal-producing system.

25. A method according to claim 21, wherein said at least one member of signal producing system comprises a polymerized lipid membrane.

26. A method according to claim 25, wherein said optical signal comprises a change in the optical properties of said lipid membrane.

27. A method according to claim 25, wherein said change in optical properties is one of a change in fluorescent emissions or a change in absorption of said lipid membrane.

28. A method according to claim 21, wherein said reagent incubation area comprises a main reagent area and an incubation area separated by a transport conduit, wherein said main reagent area comprises a first member of said signal producing system and said incubation area comprises a second member of said signal producing system.

29. A method according to claim 21, wherein said side reagent area comprises a member of said signal producing system and said method further comprises introducing liquid into said liquid addition port prior to said washing step for contact with said member of a signal producing system.

30. A disposable assay device for use in analyte detection, said device comprising:
   a sample addition port for adding a sample suspected of containing analyte, which port is in fluid communication with at least one main channel, wherein at least a portion of said main channel is a capillary and said main channel comprises:
      at least one reagent incubation area; and
      a waste area, wherein said waste area is downstream from said incubation area; and at least one side channel, said side channel comprising:
a liquid addition port and
a side reagent area downstream from said liquid addition port;
wherein (i) there is at least one reagent in the main channel or side channel, (ii), side reagent area of said side channel is in fluid communication with said main channel at a region of said main channel upstream from said reagent incubation area, and (iii) said analyte, if present, reacts with a reagent to produce a detectable signal in said reagent incubation area.

31. A detection system for use in analyte detection comprising:
an optical sensor and
an assay device comprising:
(a) a main flow path comprising:
a sample addition port for adding a sample suspected of containing an analyte,
at least one reagent incubation area downstream from said sample addition port, and
a waste area downstream from said reagent incubation area;
(b) at least one side channel, said side channel comprising:
a liquid addition port and
a side reagent area for introducing a liquid into said reagent incubation area;
(c) at least one fluid interruption means positioned along said main flow or side reagent channel upstream from said reagent incubation area; and
(d) at least one reagent in said main flow path or said side channel,
wherein said side channel is in fluid communication with said main flow path at a region of said main flow path upstream from said incubation area, and said analyte, if present, reacts with a reagent to produce a detectable signal in said reagent incubation area and said optical sensor reads said detectable signal.

32. The detection system of claim 31, further including a sample dispenser for adding sample to said sample addition port of the cartridge.

33. The detection system of claim 31, further including a liquid dispenser for adding liquid to said liquid addition port of the cartridge.

34. The detection system of claim 31, further including a temperature control associated with said cartridge for manipulating the temperature of said cartridge.

* * * * *